(12) United States Patent
Candau

(10) Patent No.: US 6,849,250 B2
(45) Date of Patent: Feb. 1, 2005

(54) SYNERGISTICALLY HIGH SPF PHOTOPROTECTIVE UV-SCREENING COMPOSITIONS COMPRISING BENZOTRIAZOLE-SUBSTITUTED SILICON/DIBENZOYLMETHANE/DIARYLBUTADIENE COMPOUNDS

(75) Inventor: Didier Candau, Bièvres (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 10/463,340

(22) Filed: Jun. 18, 2003

(65) Prior Publication Data

US 2004/0059119 A1 Mar. 25, 2004

Related U.S. Application Data

(63) Continuation of application No. PCT/FR01/03634, filed on Nov. 20, 2001.

(30) Foreign Application Priority Data

Dec. 18, 2000 (FR) .......................................... 00 16519

(51) Int. Cl.$^7$ ........................... A61K 7/42; A61K 7/44; A61K 7/00

(52) U.S. Cl. ........................... 424/59; 424/60; 424/400; 424/401

(58) Field of Search ........................... 424/59, 60, 400, 424/401

(56) References Cited

FOREIGN PATENT DOCUMENTS

DE 0967200 A1 * 6/1999
DE 1008586 A1 * 11/1999

* cited by examiner

*Primary Examiner*—Shelley A. Dodson
(74) *Attorney, Agent, or Firm*—Burns, Doane, Swecker & Mathis, L.L.P.

(57) ABSTRACT

Topically applicable, enhanced SPF cosmetic/dermatological UV-screening compositions suited for the photoprotection of the skin and/or hair, comprise, (i) at least one UV-screening benzotriazole-substituted silicon compound, as a first screening agent; (ii) at least one UV-screening dibenzoylmethane compound, as a second screening agent; (iii) at least one 4,4-diarylbutadiene compound, as a third screening agent, formulated into a topically applicable, cosmetically/dermatologically acceptable vehicle therefor.

33 Claims, No Drawings

SYNERGISTICALLY HIGH SPF PHOTOPROTECTIVE UV-SCREENING COMPOSITIONS COMPRISING BENZOTRIAZOLE-SUBSTITUTED SILICON/DIBENZOYLMETHANE/DIARYLBUTADIENE COMPOUNDS

CROSS-REFERENCE TO PRIORITY/PCT APPLICATIONS

This application claims priority under 35 U.S.C. § 119 of FR-00/16519, filed Dec. 18, 2000, and is a continuation of PCT/FR01/03634, filed Nov. 20, 2001 and designating the United States (published in the French language on Jun. 27, 2002 as WO 02/49584 A2; the title and abstract were also published in English), both hereby expressly incorporated by reference.

BACKGROUND OF THE INVENTION

1. Technical Field of the Invention

The invention relates to novel cosmetic or dermatological compositions for topical application, in particular in a regime or regimen for the photoprotection of the skin and/or the hair, comprising, formulated into a cosmetically acceptable vehicle:

(i) at least one silicon derivative with a benzotriazole functional group, as a first screening agent;
(ii) at least one dibenzoylmethane derivative, as a second screening agent;
(iii) at least one 4,4-diarylbutadiene compound, as a third screening agent.

This invention also relates to their applications in the protection of the skin and hair against the effects of ultraviolet radiation.

2. Description of Background/Related/Prior Art

It is known that light radiation with wavelengths of between 280 nm and 400 nm makes possible browning of the human epidermis and that rays with wavelengths of between 280 nm and 320 nm, known under the name of UV-B, cause erythemas and skin burns which may be harmful to the development of natural tanning; this UV-B radiation must therefore be screened out.

It is also known that UV-A rays, with wavelengths of between 320 nm and 400 nm, which cause browning of the skin, are capable of bringing about a detrimental change in the latter, in particular in the case of sensitive skin or of skin continually exposed to solar radiation. UV-A rays cause in particular a loss in the elasticity of the skin and the appearance of wrinkles, resulting in premature aging. They promote the triggering of the erythemal reaction or accentuate this reaction in some subjects and can even be the cause of phototoxic or photoallergic reactions. It is therefore desirable also to screen out UV-A radiation.

Numerous cosmetic compositions intended for the photoprotection (UV-A and/or UV-B) of the skin have been provided to date.

These antisun compositions exist fairly often in the form of an emulsion of oil-in-water type (that is to say, a cosmetically acceptable vehicle composed of a continuous aqueous dispersing phase and of a noncontinuous oily dispersed phase) which comprises, at various concentrations, one or more conventional, lipophilic and/or hydrophilic, organic screening agents capable of selectively absorbing harmful UV radiation, these screening agents (and their amounts) being selected according to the sun protection factor desired, the sun protection factor (SPF) being expressed mathematically by the ratio of the dose of UV radiation necessary to reach the erythemogenic threshold with the UV screening agent to the dose of UV radiation necessary to reach the erythemogenic threshold without UV screening agent.

Cosmetic UV screening agents formed of lipophilic silicone derivatives with a benzotriazole functional group exhibiting good screening properties, both in the region of UV-A radiation and in the region of UV-B radiation, are known in the state of the art. They are described in EP-A-0-392,883, EP-A-0-660,701, EP-A-0-708,108, EP-A-0-711,778 or EP-A-711,779.

Provision has already been made, in EP-A-0-742,003 and EP-A-0-860,165, to combine, with these silicone screening agents with a benzotriazole functional group, specific water-soluble screening agents with a sulfonic functional group, namely benzene-1,4-di(3-methylidene-10-camphorsulfonic acid) or 2-phenylbenzimidazole-5-sulfonic acid and its salts, for the purpose of producing a synergistic activity with regard to the sun protection factors. These synergistic screening systems require the use of at least one aqueous phase, which dissolves the water-soluble screening agent, and of a fatty phase for dissolving the silicone screening agent, which substantially reduces the formulation possibilities.

Suntan compositions based on 4,4-diarylbutadienes, which can comprise other additional screening agents, are known from EP-0-967,200, DE-197,46,654, DE-197,55,649, EP-1-008,586, DE-100,07,017, EP-1-133,980 and EP-1-133,981.

SUMMARY OF THE INVENTION

Following much research carried out in the abovementioned field of photoprotection, it has now unexpectedly and surprisingly been determined that a combination of three specific families of screening compounds which are already known per se in the state of the art, i.e., (1) at least one dibenzoylmethane derivative, (2) at least one benzotriazole silicon derivative and (3) at least one 4,4-diarylbutadiene, makes it possible, because of a synergistic effect, to obtain antisun compositions exhibiting markedly improved sun protection factors. Such a combination made it possible to obtain suntan compositions with markedly improved sun protection factors and in any case sun protection factors which are much greater than those which can be obtained with one or another of the screening agents used alone.

Furthermore, the specific combination of screening agents in accordance with the invention can be easily incorporated in a very wide variety of cosmetic vehicles.

This discovery is the basis of the present invention.

Thus, the present invention features novel cosmetic compositions, in particular antisun compositions, comprising, formulated into a cosmetically acceptable vehicle:

(i) at least one silicon derivative with a benzotriazole functional group, as first screening agent;
(ii) at least one dibenzoylmethane derivative, as second screening agent;
(iii) at least one 4,4-diarylbutadiene compound, as third screening agent.

The present invention also features the use of the above compositions in the manufacture of cosmetic compositions intended for the protection of the skin and/or hair against ultraviolet radiation, in particular solar radiation.

Generally, the said first, second and third screening agents are present in the compositions of the invention in a proportion producing a synergistic activity with regard to the sun protection factors conferred.

Other characteristics, aspects, embodiments and advantages of the present invention will become apparent from the detailed description which follows.

DETAILED DESCRIPTION OF BEST MODE AND SPECIFIC/PREFERRED EMBODIMENTS OF THE INVENTION

The term "4,4-diarylbutadiene compound" in accordance with the invention is understood to mean any molecule comprising at least one 4,4-diarylbutadiene chromophoric group. This molecule can be provided in the form of a simple compound, of an oligomer or of a polymer having, on the chain, grafts comprising the chromophoric group.

The silicon derivatives with a benzotriazole functional group used in the present invention are preferably silanes or siloxanes with a benzotriazole functional group comprising at least one unit of following formula (1):

in which:

$R_7$ represents an optionally halogenated $C_1$–$C_{10}$ alkyl radical or a phenyl radical or a trimethylsilyloxy radical, a is an integer ranging from 0 to 3, inclusive;

and the G symbol denotes a monovalent radical bonded directly to a silicon atom which corresponds to the following formula (2):

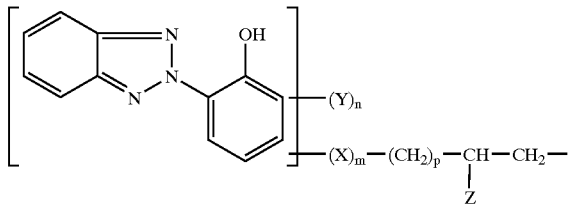

in which:

Y, which are identical or different, are chosen from $C_1$–$C_8$ alkyl radicals, halogens and $C_1$–$C_4$ alkoxy radicals, it being understood that, in the latter case, two adjacent Y radicals on the same aromatic nucleus can together form an alkylidenedioxy group in which the alkylidene group comprises from 1 to 2 carbon atoms;

X represents O or NH;

Z represents hydrogen or a $C_1$–$C_4$ alkyl radical;

n is an integer ranging from 0 to 3, inclusive;

m is 0 or 1; and p represents an integer ranging from 1 to 10, inclusive.

These compounds are described in particular in EP-A-0, 392,883, EP-A-0 660,701, EP-A-0,708,108, EP-A-0,711, 778 and EP-A-711,779.

The silicon derivatives used in the context of the present invention preferably belong to the general family of the benzotriazole silicones which is described in EP-A-0-660, 701.

A family of benzotriazole silicones which is particularly well suited for the implementation of the present invention is that comprising the compounds corresponding to the following formulae (5) and (6):

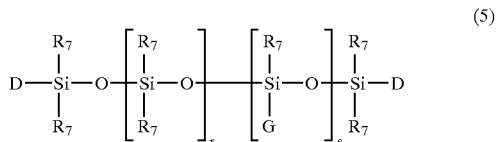

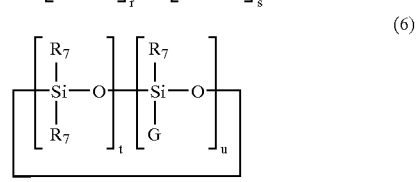

in which $R_7$, which are identical or different, are chosen from $C_1$–$C_{10}$ alkyl, phenyl, 3,3,3-trifluoropropyl and trimethylsilyloxy radicals, at least 80% by number of the $R_7$ radicals being methyl;

D, which are identical or different, are chosen from $R_7$ radicals and the G radical;

r is an integer ranging from 0 to 50, inclusive, and s is an integer ranging from 0 to 20, inclusive, and, if s=0, at least one of the two D symbols denotes G;

u is an integer ranging from 1 to 6, inclusive, and t is an integer ranging from 0 to 10, inclusive, it being understood that t+u is equal to or greater than 3;

and the G symbol corresponds to the above formula (2).

As seen from the formula (2) given above, the attachment of the —(X)$_m$—(CH$_2$)$_p$—CH(Z)-CH$_2$— link to the benzotriazole unit, which therefore ensures that the said benzotriazole unit is connected to the silicon atom of the silicone chain, can, according to the present invention, take place in all the available positions offered by the two aromatic nuclei of the benzotriazole:

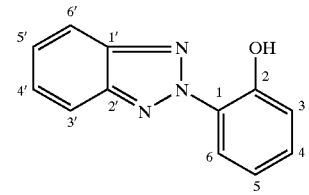

Preferably, this attachment takes place in the 3, 4 or 5 position (aromatic nucleus carrying the hydroxyl functional group) or 4' position (benzene nucleus adjacent to the triazole ring) and more preferably still in the 3, 4 or 5 position. In a preferred embodiment of the invention, the attachment takes place in the 3 position.

Likewise, the attachment of the Y substituent unit or units can take place in all the other positions available within the benzotriazole. However, this attachment preferably takes place in the 3, 4, 4', and/or 6 position. In a preferred embodiment of the invention, the attachment of the Y unit takes place in the 5 position.

In the above formulae (5) and (6), the alkyl radicals can be linear or branched and can be chosen in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred $R_7$ alkyl radicals according to the invention are the methyl, ethyl, propyl, n-butyl, n-octyl and 2-ethylhexyl radicals. More preferably still, the $R_7$ radicals are all methyl radicals.

Among the compounds of formulae (5) and (6) above, it is preferable to employ those corresponding to the formula (5), that is to say diorganosiloxanes with a short linear chain.

Among the compounds of formula (5) above, it is preferable to employ those in which the D radicals are both $R_7$ radicals.

Preference is more particularly given, among the linear diorganosiloxanes coming within the scope of the present invention, to statistical derivatives or alternatively block-defined derivatives exhibiting at least one and more preferably still all of the following characteristics:

D is an $R_7$ radical;
$R_7$ is alkyl and more preferably still is methyl;
r ranges from 0 to 15, inclusive; s ranges from 1 to 10, inclusive;
n is not zero and preferably is equal to 1 and Y is then chosen from methyl, tert-butyl or $C_1$–$C_4$ alkoxy;
Z is hydrogen or methyl;
m=0 or [m=1 and X=O];
p is equal to 1.

A family of benzotriazole silicones which is particularly well suited to the invention is that defined by the following general formula (7):

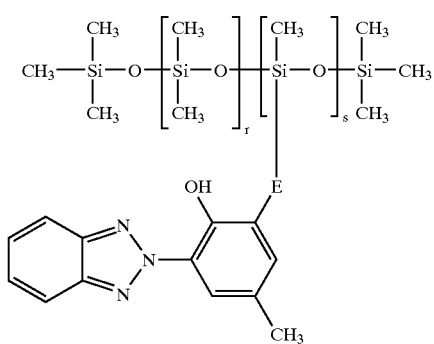

with $0 \leq r \leq 10$, $1 \leq s \leq 10$, and where E represents the divalent radical:

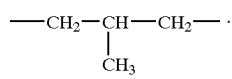

In a particularly preferred embodiment of the invention, the benzotriazole silicone is the compound Drometrizole Trisiloxane (CTFA name) corresponding to the following formula:

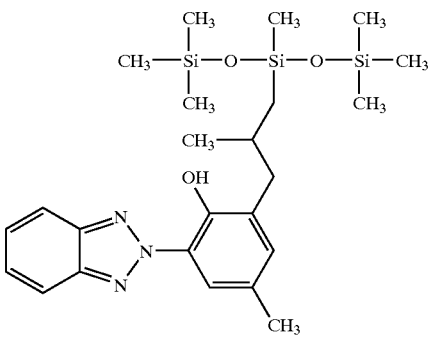

Processes suitable for the preparation of the products of formulae (1), (5), (6) and (7) above are described in U.S. Pat. Nos. 3,220,972, 3,697,473, 4,340,709, 4,316,033, and 4,328,346 and in EP-A-0-392,883 and EP-A-0-742,003.

The silicon derivative with a benzotriazole functional group can be present in the compositions according to the invention at contents ranging from 0.5% to 15%, preferably ranging from 1% to 10%, by weight, and more particularly from 2% to 8% by weight, still with respect to the total weight of the composition.

As indicated above, the dibenzoylmethane derivatives of the present invention are products already well known per se and described in particular in FR-A-2-326,405, FR-A-2-440, 933 and EP-A-0-114,607, the teachings of which documents are, in so far as they affect the actual definition of these products, entirely included by way of references in the present description.

Mention may in particular be made, without implied limitation, among the dibenzoylmethane derivatives more particularly targeted by the present invention, of:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Preference is very particularly given, according to the present invention, among the dibenzoylmethane derivatives mentioned above, to the use of 4-tert-butyl-4'-methoxydibenzoylmethane, in particular that provided for sale under the trade name "Parsol 1789" by Hoffman-LaRoche, this screening agent corresponding to the following expanded formula (I):

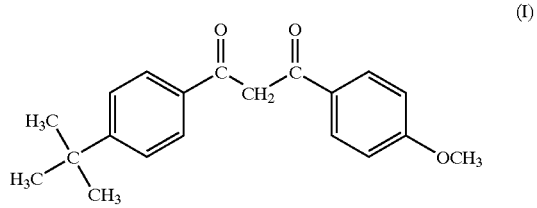

Another preferred dibenzoylmethane derivative according to the present invention is 4-isopropyldibenzoylmethane, a screening agent sold under the name of "Eusolex 8020" by Merck and corresponding to the following expanded formula (II):

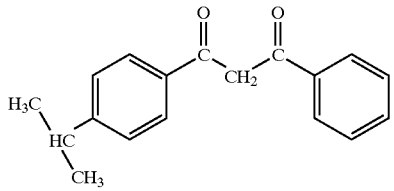

(II)

The dibenzoylmethane derivative or derivatives are present in the compositions in accordance with the invention at contents preferably ranging from 0.5% to 15% by weight and more preferably from 1% to 10% by weight and more particularly from 2% to 8% by weight with respect to the total weight of the composition.

The choice may be made, among the preferred 4,4-diarylbutadiene compounds in accordance with the invention, of the compounds corresponding to the following formula (III):

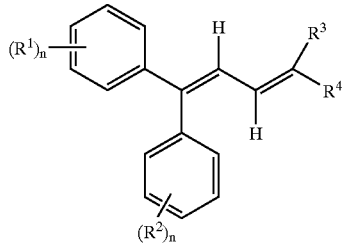

(III)

in which the diene system has the Z,Z; Z,E; E,Z or E,E configuration or is composed of mixtures of the said configurations, and where:

$R^1$ and $R^2$, which are identical or different, denote hydrogen; a linear or branched $C_1$–$C_{20}$ alkyl radical; a $C_2$–$C_{10}$ alkenyl radical; a $C_1$–$C_{12}$ alkoxy radical; a $C_3$–$C_{10}$ cycloalkyl radical; a $C_3$–$C_{10}$ cycloalkenyl radical; a linear or branched $C_1$–$C_{20}$ alkoxycarbonyl radical; a linear or branched $C_1$–$C_{12}$ monoalkylamino radical; a linear or branched di($C_1$–$C_{12}$)alkylamino radical; an aryl radical; a heteroaryl radical or a water-solubilizing substituent chosen from a carboxylate group, a sulfonate group or an ammonium residue;

$R^3$ denotes a $COOR^5$, $COR^5$, $CONR^5R^6$ or CN group; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; a $C_6$–$C_{18}$ aryl radical; or a $C_3$–$C_7$ heteroaryl radical;

$R^4$ denotes a $COOR^6$, $COR^6$, $CONR^5R^6$ or CN group; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; or a heteroaryl radical;

$R^5$ and $R^6$, which are identical or different, denote hydrogen; $[V]_o$—$R^7$; $C_1$–$C_6$-alkylene-$SO_3U$; $C_1$–$C_6$-alkylene-$PO_3U$; $C_1$–$C_6$-alkylene-$N(R^8)_3^+A^-$; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; or a heteroaryl radical;

V denotes a —$CH_2$—$CH_2$—W—, —$CH_2CH_2CH_2W$—, —$CH(CH_3)$—$CH_2$—W—, —$CH_2$—$CH_2$—$CH_2$—$CH_2$—W— or —$CH_2$—$CH(CH_2CH_3)$—W— group;

A denotes Cl, Br, I or $SO_4R^9$;

U denotes hydrogen, $Na^+$, $K^+$, $Mg^{2+}$, $Ca^{2+}$, $Li^+$, $Al^{3+}$ or —$N(R^8)_4^+$;

W denotes O or NH;

$R^7$ and $R^8$, which are identical or different, denote hydrogen; a linear or branched $C_1$–$C_6$ alkyl radical; a linear or branched $C_2$–$C_6$ alkenyl radical; or a linear or branched $C_1$–$C_6$ acyl radical;

$R^9$ denotes hydrogen; a linear or branched $C_1$–$C_6$ alkyl radical; or a $C_2$–$C_6$ alkenyl radical;

l varies from 1 to 3;

o varies from 0 to 150.

Mention may be made, as alkyl radicals, of, for example: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-icosyl.

Mention may be made, as $C_2$–$C_{10}$ alkenyl groups, of, for example: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,1-dimethylbutenyl, 1,3-dimethylbutenyl, 2,2-dimethylbutenyl, 2,3-dimethylbutenyl, 3,3-dimethylbutenyl, 1-ethylbutenyl, 2-ethylbutenyl, 1,1,2-trimethylpropenyl, 1,2,2-trimethylpropenyl, 1-ethyl-1-methylpropenyl, 1-ethyl-2-methylpropenyl, n-heptenyl, n-octenyl, n-nonenyl or n-decenyl.

Mention may be made, as $C_1$–$C_{12}$ alkoxy radicals for the $R^1$ and $R^2$ radicals, of: methoxy, n-propoxy, 1-methylpropoxy, 1-methylethoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy or 2-ethylhexoxy.

Mention may be made, as $C_3$–$C_{10}$ cycloalkyl radicals for the $R^6$ and $R^7$ radicals, of, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Mention may be made, as $C_3$–$C_{10}$ cycloalkenyl radicals having one or more double bonds for the $R^6$ and $R^7$ radicals, of: cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals can comprise one or more substituents (preferably from 1 to 3) chosen, for example, from halogen, such as chlorine, fluorine or bromine; cyano; nitro; amino; $C_1$–$C_4$ alkylamino; di($C_1$–$C_4$) alkylamino; $C_1$–$C_4$ alkyl; $C_1$–$C_4$ alkoxy; or hydroxyl. They can also comprise from 1 to 3 heteroatoms, such as sulfur, oxygen or nitrogen, the free valences of which can be satisfied by a hydrogen or a $C_1$–$C_4$ alkyl radical.

Mention may be made, as acyl radicals, of, for example, formyl, acetyl, propionyl or n-butyryl.

The bicycloalkyl or bicycloalkenyl groups are chosen, for example, from bicyclic terpenes, such as pinane, bornane, pinene or camphor or adamantane derivatives.

The aryl groups are preferably chosen from phenyl or naphthyl rings which can comprise one or more substituents (preferably from 1 to 3) chosen, for example, from halogen, such as chlorine, fluorine or bromine; cyano; nitro; amino; $C_1$–$C_4$ alkylamino; di($C_1$–$C_4$) alkylamino; $C_1$–$C_4$ alkyl; $C_1$–$C_4$ alkoxy; or hydroxyl. Preference is more particularly given to phenyl, methoxyphenyl and naphthyl.

The heteroaryl groups generally comprise one or more heteroatoms chosen from sulfur, oxygen or nitrogen.

The water-solubilizing groups are, for example, carboxylate or sulfonate groups and more particularly their salts with physiologically acceptable cations, such as alkali metal salts or trialkylammonium salts, such as tri(hydroxyalkyl) ammonium or 2-methylpropan-1-ol-2-ammonium salts. Mention may also be made of ammonium groups, such as alkylammoniums, and their salified forms with physiologically acceptable anions.

The preferred compounds of formula (III) are chosen from those of following formula (IIIa):

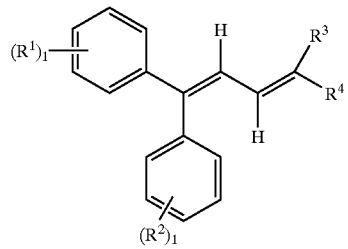

(IIIa)

in which the diene system has the Z,Z; Z,E; E,Z or E,E configuration or is composed of mixtures of the said configurations, and where:

$R^1$ and $R^2$, which are identical or different, denote hydrogen; a $C_1$–$C_8$ alkyl radical; a $C_1$–$C_8$ alkoxy radical; or a water-solubilizing substituent chosen from a carboxylate group, a sulfonate group or an ammonium residue;
$R^3$ denotes a $COOR^5$, $CONR^5R^6$ or CN group;
$R^4$ denotes a $COOR^6$ or $CONR^5R^6$ group;
$R^5$ denotes hydrogen; $[V]_o$—$R^7$; $C_1$–$C_6$-alkylene-$SO_3U$; or $C_1$–$C_6$-alkylene-$N(R^8)_3{}^+A^-$;
$R^6$ denotes $[V]_o$—$R^7$; $C_1$–$C_6$-alkylene-$SO_3U$; or $C_1$–$C_6$-alkylene-$N(R^8)_3{}^+A^-$;
V denotes a —$CH_2$—$CH_2$—O—, —$CH_2CH_2CH_2O$— or —$CH(CH_3)$—$CH_2$—O— group;
A denotes Cl, Br, I or $SO_4R^9$;
U denotes hydrogen, $Na^+$, $K^+$, $Mg^{2+}$, $Ca^{2+}$, $Li^+$, $Al^{3+}$ or —$N(R^8)_4{}^+$;
$R^7$, $R^8$ and $R^9$, which are identical or different, denote hydrogen or a linear or branched $C_1$–$C_3$ alkyl radical;
l varies from 1 to 3;
o varies from 0 to 50.

The even more preferential compounds of formula (III) are chosen from those corresponding to the following formula (IIIb):

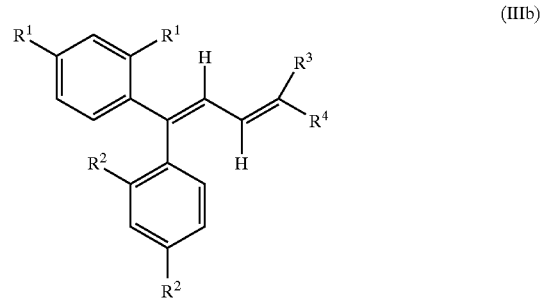

(IIIb)

in which the diene system has the Z,Z; Z,E; E,Z or E,E configuration or is composed of mixtures of the said configurations, and where:

$R^1$ and $R^2$, which are identical or different, denote hydrogen; a $C_1$–$C_8$ alkyl radical; or a $C_1$–$C_8$ alkoxy radical;
$R^3$ denotes a $COOR^5$, $CONR^5R^6$ or CN group;
$R^4$ denotes a $COOR^6$ or $CONR^5R^6$ group;
$R^5$ denotes hydrogen; $[V]_o$—$R^7$; $C_1$–$C_6$-alkylene-$SO_3U$; or $C_1$–$C_6$-alkylene-$N(R^8)_3{}^+A^-$;
$R^6$ denotes $[V]_o$—$R^7$; $C_1$–$C_6$-alkylene-$SO_3U$; or $C_1$–$C_6$-alkylene-$N(R^8)_3{}^+A^-$;
V denotes a —$CH_2$—$CH_2$—O—, —$CH_2CH_2CH_2O$— or —$CH(CH_3)$—$CH_2$—O— group;
A denotes Cl, Br, I or $SO_4R^9$;
U denotes hydrogen, $Na^+$, $K^+$, $Mg^{2+}$, $Ca^{2+}$, $Li^+$, $Al^{3+}$ or —$N(R^8)_4{}^+$;
$R^7$, $R^8$ and $R^9$, which are identical or different, denote hydrogen or a linear or branched $C_1$–$C_3$ alkyl radical;
o varies from 0 to 50.

The even more preferential compounds of formula (III) are chosen from those corresponding to the following formula (IIIc):

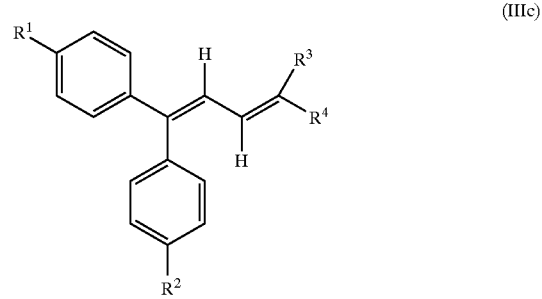

(IIIc)

in which the diene system has the Z,Z; Z,E; E,Z or E,E configuration or is composed of mixtures of the said configurations, and where:

$R^1$ and $R^2$, which are identical or different, denote hydrogen; a $C_1$–$C_8$ alkyl radical; or a $C_1$–$C_8$ alkoxy radical;
$R^3$ denotes a $COOR^5$, $CONR^5R^6$ or CN group;
$R^4$ denotes a $COOR^6$ or $CONR^5R^6$ group;
$R^5$ denotes hydrogen; $[V]_o$—$R^7$; $C_1$–$C_6$-alkylene-$SO_3U$; or $C_1$–$C_6$-alkylene-$N(R^8)_3{}^+A^-$;
$R^6$ denotes $[V]_o$—$R^7$; $C_1$–$C_6$-alkylene-$SO_3U$; or $C_1$–$C_6$-alkylene-$N(R^8)_3{}^+A^-$;

V denotes a —CH$_2$—CH$_2$—O—, —CH$_2$CH$_2$CH$_2$O— or —CH(CH$_3$)—CH$_2$—O— group;

A denotes Cl, Br, I or SO$_4$R$^9$;

U denotes hydrogen, Na$^+$, K$^+$, Mg$^{2+}$, Ca$^{2+}$, Li$^+$, Al$^{3+}$ or —N(R$^8$)$_4^+$;

R$^7$, R$^8$ and R$^9$, which are identical or different, denote hydrogen or a linear or branched C$_1$–C$_3$ alkyl radical;

o varies from 0 to 50.

The even more particularly preferred compounds of formula (III) are chosen from the following compounds:

(8)
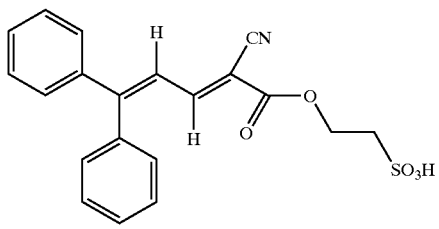

(9)
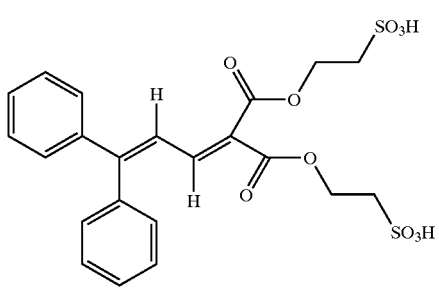

(10)
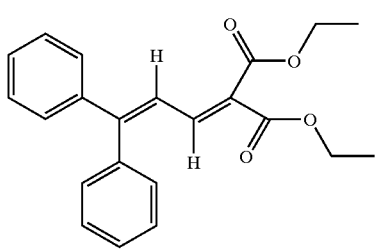

(11)
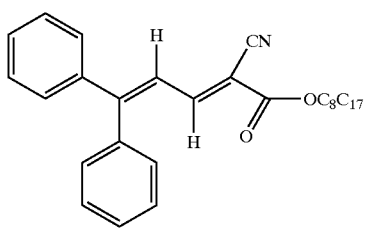

(12)
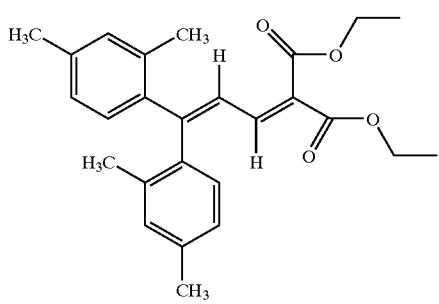

The compounds of formula (III) as defined above are known per se and their structures and their syntheses are described in EP-0-967,200, DE-197,46,654 and DE-197,55,649 (which form an integral part of the content of the description).

Mention may also be made, among the preferred 4,4-diarylbutadiene compounds in accordance with the invention, of the oligomers corresponding to the following formula (IV):

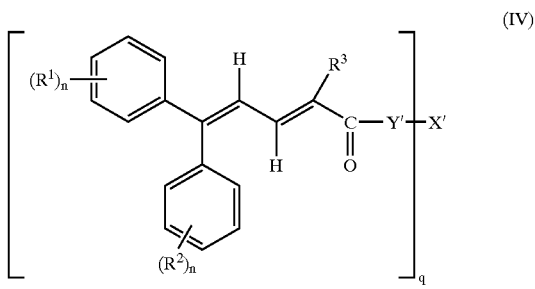

(IV)

in which the diene system has the Z,Z; Z,E; E,Z or E,E configuration or is composed of mixtures of the said configurations, and where:

R$^1$, R$^2$, R$^3$ and n have the same meanings indicated in the preceding formula (III);

Y' denotes an —O— or —NR$^{10}$— group;

R$^{10}$ denotes hydrogen; a linear or branched C$_1$–C$_{20}$ alkyl radical; a C$_2$–C$_{10}$ alkenyl radical; a C$_3$–C$_{10}$ cycloalkyl radical; a C$_7$–C$_{10}$ bicycloalkyl radical; a C$_3$–C$_{10}$ cycloalkenyl radical; a C$_7$–C$_{10}$ bicycloalkenyl radical; an aryl radical; or a heteroaryl radical;

X' denotes a linear or branched, aliphatic or cycloaliphatic, polyol residue comprising 2 to 10 hydroxyl groups and with a valency of q; it being possible for the carbonaceous chain of the said residue to be interrupted by one or more sulfur or oxygen atoms; one or more imine groups; or one or more C$_1$–C$_4$ alkylimine groups;

q varies from 2 to 10.

X' is a polyol residue comprising from 2 to 10 hydroxyl groups and in particular:

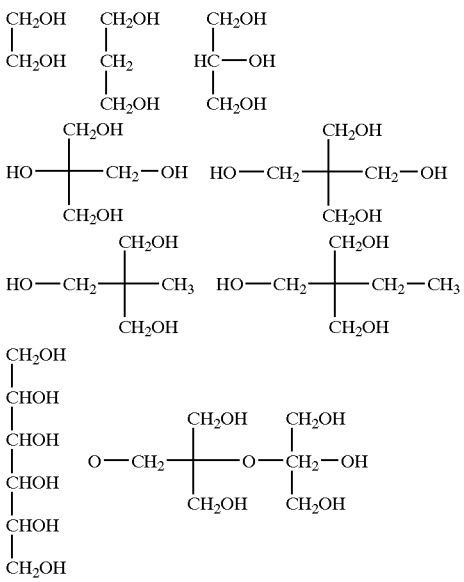

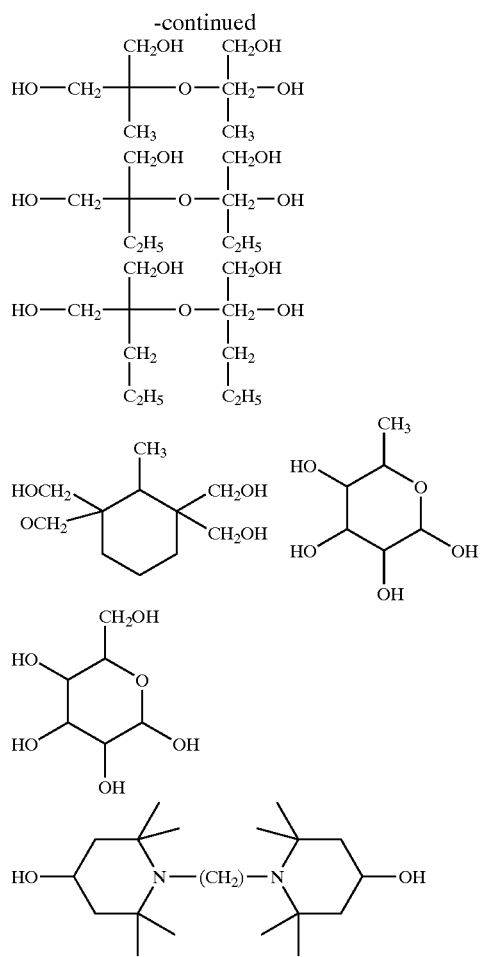

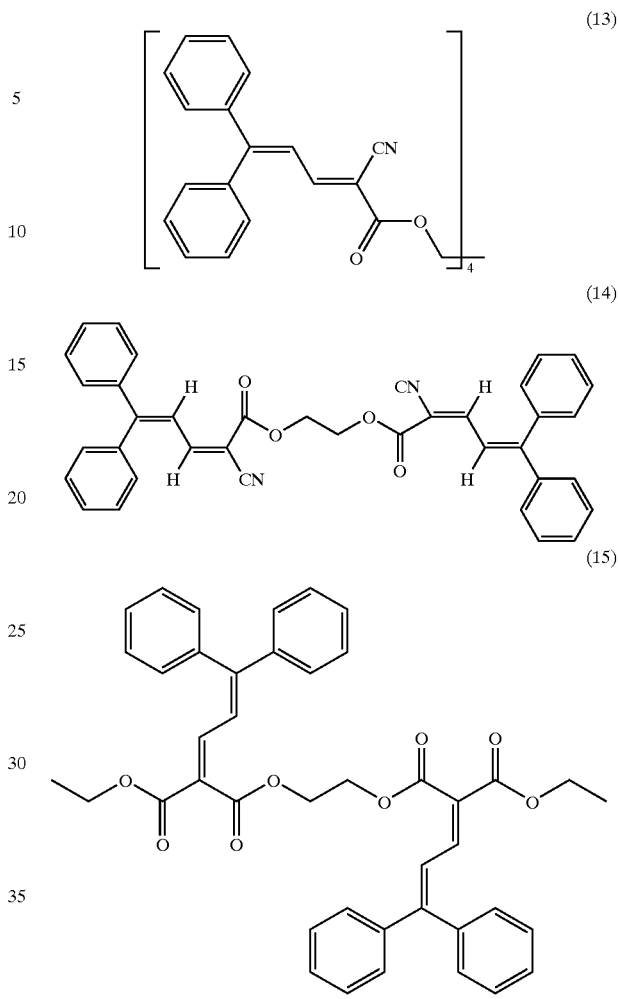

The more preferential compounds of formula (IV) are those for which:

R¹ and R², which are identical or different, denote hydrogen; a $C_1$–$C_{12}$ alkyl radical; a $C_1$–$C_8$ alkoxy radical; or a water-solubilizing substituent chosen from a carboxylate group, a sulfonate group or an ammonium residue;

R³ denotes a $COOR^5$, $CONR^5R^6$ or CN group; a $C_3$–$C_{10}$ cycloalkyl radical; or a $C_7$–$C_{10}$ bicycloalkyl radical;

R⁵ and R⁶, which are identical or different, denote a linear or branched $C_1$–$C_{20}$ alkyl radical; a $C_3$–$C_{10}$ cycloalkyl radical; a $C_7$–$C_{10}$ bicycloalkyl radical; or an optionally substituted naphthyl or phenyl;

X' denotes a polyol residue comprising from 2 to 6 hydroxyl groups and more particularly from 2 to 4.

The even more preferential compounds of formula (IV) are those for which:

X' denotes an ethanol or pentaerythritol residue.

The even more particularly preferred compounds of formula (IV) are chosen from the following compounds:

The compounds of formula (IV) as defined above are known per se and their structures and their synthesis are described in EP-A-1-008,586 (which forms an integral part of the content of the description).

The 4,4'-diarylbutadiene compounds in accordance with the invention are generally present in the composition of the invention at contents which preferably vary from 0.5% to 15% by weight and more preferably from 1% to 10% by weight and more particularly from 2% to 8% by weight with respect to the total weight of the composition.

In addition, the compositions in accordance with the invention can comprise other additional organic UV screening agents which are active in the UV-A and/or UV-B regions (absorbers) and which are soluble in water or fats or else insoluble in the cosmetic solvents commonly used.

The additional organic UV screening agents are chosen in particular from anthranilates; cinnamic derivatives; salicylic derivatives; camphor derivatives, other than p-methylbenzylidenecamphor; triazine derivatives, such as those described in U.S. Pat. No. 4,367,390, EP-863,145, EP-517,104, EP-570,838, EP-796,851, EP-775,698, EP-878,469 and EP-933,376; benzophenone derivatives; β,β-diphenylacrylate derivatives; benzotriazole derivatives; benzalmalonate derivatives; benzimidazole derivatives; imidazolines; bisbenzoazolyl derivatives as described in EP-669,323 and U.S. Pat. No. 2,463,264; p-aminobenzoic acid (PABA) derivatives; methylenebis (hydroxyphenylbenzotriazole) derivatives as described in U.S. Pat. Nos. 5,237,071, 5,166,355, GB-2-303,549, DE-197,26,184 and EP-893,119; screening polymers and screening silicones other than those of the invention, such as those described in particular in WO 93/04665; or dimers derived from α-alkylstyrene, such as those described in DE-198,55,649.

Mention may be made, as examples of additional organic screening agents which are active in the UV-A and/or UV-B regions, of, denoted below under their INCI names:

Para-Aminobenzoic Acid Derivatives:

PABA,
Ethyl PABA,
Ethyl Dihydroxypropyl PABA,
Ethylhexyl Dimethyl PABA, sold in particular under the name "Escalol 507" by ISP,
Glyceryl PABA,
PEG-25 PABA, sold under the name "Uvinul P25" by BASF, Salicylic Derivatives:

Homosalate, sold under the name "Eusolex HMS" by Rona/EM Industries,
Ethylhexyl Salicylate, sold under the name "Neo Heliopan OS" by Haarmann and Reimer,
Dipropyleneglycol Salicylate, sold under the name "Dipsal" by Scher,
TEA Salicylate, sold under the name "Neo Heliopan TS" by Haarmann and Reimer, Cinnamic Derivatives:

Ethylhexyl Methoxycinnamate, sold in particular under the trademark "Parsol MCX" by Hoffmann-LaRoche,
Isopropyl Methoxy cinnamate,
Isoamyl Methoxy cinnamate, sold under the trademark "Neo Heliopan E 1000" by Haarmann and Reimer,
Cinoxate,
DEA Methoxycinnamate,
Diisopropyl Methylcinnamate,
Glyceryl Ethylhexanoate Dimethoxycinnamate, β,β-Diphenylacrylate Derivatives:

Octocrylene, sold in particular under the trademark "Uvinul N539" by BASF,
Etocrylene, sold in particular under the trademark "Uvinul N35" by BASF, Benzophenone Derivatives:

Benzophenone-1, sold under the trademark "Uvinul 400" by BASF,
Benzophenone-2, sold under the trademark "Uvinul D50" by BASF,
Benzophenone-3 or Oxybenzone, sold under the trademark "Uvinul M40" by BASF,
Benzophenone-4, sold under the trademark "Uvinul MS40" by BASF,
Benzophenone-5,
Benzophenone-6, sold under the trademark "Helisorb 11" by Norquay,
Benzophenone-8, sold under the trademark "Spectra-Sorb UV-24" by American Cyanamid,
Benzophenone-9, sold under the trademark "Uvinul DS-49" by BASF,
Benzophenone-12, Benzylidenecamphor Derivatives:

3-Benzylidene camphor, manufactured under the name "Mexoryl SD" by Chimex,
Benzylidene Camphor Sulfonic Acid, manufactured under the name "Mexoryl SL" by Chimex,
Camphor Benzalkonium Methosulfate, manufactured under the name "Mexoryl SO" by Chimex,
Terephthalydidene Dicamphor Sulfonic Acid, manufactured under the name "Mexoryl SX" by Chimex,
Polyacrylamidomethyl Benzylidene Camphor, manufactured under the name "Mexoryl SW" by Chimex, Benzimidazole Derivatives:

Phenylbenzimidazole Sulfonic Acid, sold in particular under the trademark "Eusolex 232" by Merck,
Disodium Phenyl Dibenzimidazole Tetrasulfonate, sold under the trademark "Neo Heliopan AP" by Haarmann and Reimer, Triazine Derivatives:

Anisotriazine, sold under the trademark "Tinosorb S" by Ciba Specialty Chemicals,
Ethylhexyl triazone, sold in particular under the trademark "Uvinul T150" by BASF,
Diethylhexyl Butamido Triazone, sold under the trademark "Uvasorb HEB" by Sigma 3V,
2,4,6-tris(diisobutyl 4'-aminobenzalmalonate)-s-triazine, Phenylbenzotriazole Derivatives:

Drometrizole Trisiloxane, sold under the name "Silatrizole" by Rhodia Chimie,
Methylene bis-Benzotriazolyl Tetramethylbutyl-phenol, sold in the solid form under the trademark "Mixxim BB/100" by Fairmount Chemical or in the micronized form in aqueous dispersion under the trademark "Tinosorb M" by Ciba Specialty Chemicals, Anthranilic Derivatives:

Menthyl anthranilate, sold under the trademark "Neo Heliopan MA" by Haarmann and Reimer, Imidazoline Derivatives:

Ethylhexyl Dimethoxybenzylidene Dioxoimidazoline Propionate,

Benzalmalonate Derivatives:

Polyorganosiloxane comprising a benzalmalonate functional group, sold under the trademark "Parsol SLX" by Hoffmann-LaRoche, and their mixtures.

The soluble organic UV screening agents which are more particularly preferred are chosen from the following compounds:

Ethylhexyl Salicylate,
Ethylhexyl Methoxycinnamate,
Octocrylene,
Phenylbenzimidazole Sulfonic Acid, Benzophenone-3,
Benzophenone-4,
Benzophenone-5,
4-Methylbenzylidene camphor,
Disodium Phenyl Dibenzimidazole Tetrasulfonate,
Anisotriazine,
Ethylhexyl triazone,
Diethylhexyl Butamido Triazone,
2,4,6-Tris(diisobutyl 4'-aminobenzalmalonate)-s-triazine,
Methylene bis-Benzotriazolyl Tetramethylbutyl-phenol, and their mixtures.

The cosmetic compositions according to the invention can also comprise pigments or alternatively nanopigments (mean size of the primary particles: generally between 5 nm and 100 nm, preferably between 10 nm and 50 nm) formed from coated or uncoated metal oxides, such as, for example, nanopigments formed from titanium oxide (amorphous or crystallized in the rutile and/or anatase form), iron oxide, zinc oxide, zirconium oxide or cerium oxide, which are all UV photoprotective agents well known per se. Conventional coating agents are, furthermore, alumina and/or aluminum stearate. Such coated or uncoated metal oxide nanopigments are described in particular in EP-A-0-518,772 and EP-A-0-518,773.

The compositions according to the invention can also comprise agents for the artificial tanning and/or browning of the skin (self-tanning agents), such as, for example, dihydroxyacetone (DHA).

The compositions of the invention can additionally comprise conventional cosmetic adjuvants chosen in particular from fatty substances, organic solvents, ionic or nonionic thickeners, softeners, antioxidants, agents for combating free radicals, opacifiers, stabilizers, emollients, silicones, $\alpha$-hydroxy acids, antifoaming agents, moisturizing agents, vitamins, insect repellents, fragrances, preservatives, surfactants, anti-inflammatories, substance P antagonists, fillers, polymers, propellants, basifying or acidifying agents, colorants or any other ingredient commonly used in cosmetics, in particular for the manufacture of antisun compositions in the form of emulsions.

The fatty substances can be composed of an oil or a wax or their mixtures. The term "oil" is understood to mean a compound which is liquid at ambient temperature. The term "wax" is understood to mean a compound which is solid or substantially solid at ambient temperature and for which the melting point is generally greater than 35° C. They also comprise fatty acids, fatty alcohols and esters of fatty acids which are linear or cyclic, such as derivatives of benzoic acid, trimellitic acid and hydroxybenzoic acid.

Mention may be made, as oils, of mineral oils (liquid paraffin); vegetable oils (sweet almond, macadamia, blackcurrant seed or jojoba oil); synthetic oils, such as perhydrosqualene, fatty alcohols, acids or esters (such as the $C_{12}$–$C_{15}$ alkyl benzoate sold under the trademark "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; or polyalkylenes.

Mention may be made, as waxy compounds, of paraffin wax, carnauba wax, beeswax or hydrogenated castor oil.

Of course, a person skilled in the art will take care to choose this or these optional additional compounds and/or their amounts so that the advantageous properties, in particular the synergy of the protection factors, intrinsically attached to the compositions in accordance with the invention are not, or not substantially, detrimentally affected by the envisaged addition or additions.

The compositions of the invention can be prepared according to techniques well known to a person skilled in the art, in particular those intended for the preparation of emulsions of oil-in-water or water-in-oil type.

These compositions can be provided in particular in the form of a simple or complex emulsion (O/W, W/O, O/W/O or W/O/W), such as a cream, a milk, a gel or a cream gel, of a powder or of a solid tube and can optionally be packaged as an aerosol and provided in the form of a foam or spray.

When it is a question of an emulsion, the aqueous phase of the latter can comprise a nonionic vesicular dispersion prepared according to known processes (Bangham, Standish and Watkins, J. Mol. Biol., 13, 238 (1965), FR-2-315,991 and FR-2-416,008).

The cosmetic composition of the invention can be used as a composition for protecting the human epidermis or the hair against ultraviolet rays, as an antisun composition or as a make-up product.

When the cosmetic composition according to the invention is used in a regime or regimen for the protection of the human epidermis against UV rays or as an antisun composition, it can be provided in the form of a suspension or dispersion in solvents or fatty substances, in the form of a nonionic vesicular dispersion or in the form of an emulsion, preferably of oil-in-water type, such as a cream or a milk, in the form of an ointment, gel, cream gel, solid tube, powder, stick, aerosol foam or spray.

When the cosmetic composition according to the invention is used for the protection of the hair against UV rays, it can be provided in the form of a shampoo, lotion, gel, emulsion or nonionic vesicular dispersion and can constitute, for example, a rinse-out composition, to be applied before or after shampooing, before or after dyeing or bleaching, and before, during or after perming or hair straightening, a styling or treating lotion or a styling or treating gel, a lotion or a gel for blow-drying or hair setting, or a composition for perming or straightening, dyeing or bleaching the hair.

When the composition is used as a product for making up the eyelashes, eyebrows or skin, such as a treatment cream for the epidermis, foundation, lipstick tube, eyeshadow, face powder, mascara or eyeliner, it can be provided in the anhydrous or aqueous, pasty or solid form, such as oil-in-water or water-in-oil emulsions, nonionic vesicular dispersions, or suspensions.

By way of indication, for the antisun formulations in accordance with the invention which exhibit a vehicle of oil-in-water emulsion type, the aqueous phase (comprising in particular the hydrophilic screening agents) generally represents from 50% to 95% by weight, preferably from 70% to 90% by weight, with respect to the entire formulation, the oily phase (comprising in particular the lipophilic screening agents) from 5% to 50% by weight, preferably from 10% to 30% by weight, with respect to the entire formulation, and the (co)emulsifier(s) from 0.5% to 20% by weight, preferably from 2% to 10% by weight, with respect to the entire formulation.

As indicated above, the present invention features the use of a composition as defined above in the manufacture of a cosmetic or dermatological composition intended for the protection of the skin and/or hair against ultraviolet radiation, in particular solar radiation.

In order to further illustrate the present invention and the advantages thereof, the following specific examples are given, it being understood that same are intended only as illustrative and in nowise limitative.

In said examples to follow, all parts and percentages are given by weight, unless otherwise indicated.

The following Tables 1–5 report Examples 1–5, specific compositions according to the invention.

TABLE 1

| COMPOSITION | EXAMPLE 1 |
| --- | --- |
| Glycerol mono/distearate/polyethylene glycol (100 EO) stearate mixture (Arlacel 165 FL, ICI) | 2 |
| Stearyl alcohol (Lanette 18, Henkel) | 1 |
| Palm oil stearic acid (Stéarine TP, Stéarinerie Dubois) | 2.5 |
| Polydimethylsiloxane (Dow Corning 200 Fluid, Dow Corning) | 0.5 |
| $C_{12}/C_{15}$ Alkyl benzoate (Witconol TN, Witco) | 20 |
| Triethanolamine | 0.5 |
| Butyl Methoxydibenzoylmethane (Parsol 1789, Hoffmann-LaRoche) | 2 |
| Drometrizole Trisiloxane (Silatrizole, Rhodia Chimie) | 5 |
| Compound of formula (8) | 8 |
| Glycerol | 4 |
| Triethanolamine | 0.3 |
| Polyacrylic acid (Synthalen K, 3V) | 0.4 |
| Preservatives | q.s |
| Demineralized water q.s. for | 100 g |

TABLE 2

| COMPOSITION | EXAMPLE 2 |
| --- | --- |
| 80/20 Mixture of cetearyl alcohol and of oxyethylenated (33 EO) cetearyl alcohol (Sinnowax AO, Henkel) | 7 |
| Mixture of glycerol mono- and distearate (Cerasynt SD-V, ISP) | 2 |
| Cetyl alcohol | 1.5 |
| Polydimethylsiloxane (Dow Corning 200 Fluid, Dow Corning) | 1.5 |
| Liquid petrolatum | 15 |
| Butyl Methoxydibenzoylmethane (Parsol 1789, Hoffmann-LaRoche) | 3 |
| Compound of formula (10) | 6 |
| Drometrizole Trisiloxane (Silatrizole, Rhodia Chimie) | 3 |
| Glycerol | 15 |
| Preservatives | q.s. |
| Demineralized water q.s. for | 100 g |

TABLE 3

| COMPOSITION | EXAMPLE 3 |
| --- | --- |
| Glycerol mono/distearate/polyethylene glycol (100 EO) stearate mixture (Arlacel 165 FL, ICI) | 2 |
| Stearyl alcohol (Lanette 18, Henkel) | 1 |
| Palm oil stearic acid (Stéarine TP, Stéarinerie Dubois) | 2.5 |
| Polydimethylsiloxane (Dow Corning 200 Fluid, Dow Corning) | 0.5 |
| $C_{12}/C_{15}$ Alkyl benzoate (Witconol TN, Witco) | 20 |
| Triethanolamine | 0.5 |
| Butyl Methoxydibenzoylmethane (Parsol 1789, Hoffmann-LaRoche) | 2 |
| Drometrizole Trisiloxane (Silatrizole, Rhodia Chimie) | 6 |
| Compound of formula (11) | 8 |
| Oxybenzone (Uvinul M40, BASF) | 10 |
| Glycerol | 4 |
| Triethanolamine | 0.3 |
| Polyacrylic acid (Synthalen K, 3V) | 0.4 |
| Preservatives | q.s |
| Demineralized water q.s. for | 100 g |

TABLE 4

| COMPOSITION | EXAMPLE 4 |
| --- | --- |
| 80/20 Mixture of cetearyl alcohol and of oxyethylenated (33 EO) cetearyl alcohol (Sinnowax AO, Henkel) | 7 |
| Mixture of glycerol mono- and distearate (Cerasynt SD-V, ISP) | 2 |
| Cetyl alcohol | 1.5 |
| Polydimethylsiloxane (Dow Corning 200 Fluid, Dow Corning) | 1.5 |
| Liquid petrolatum | 15 |
| Butyl Methoxydibenzoylmethane (Parsol 1789, Hoffmann-LaRoche) | 2 |
| Compound of formula (13) | 6 |
| Drometrizole Trisiloxane (Silatrizole, Rhodia Chimie) | 6 |
| Glycerol | 15 |
| Preservatives | q.s. |
| Demineralized water q.s. for | 100 g |

TABLE 5

| COMPOSITION | EXAMPLE 5 |
| --- | --- |
| Glycerol mono/distearate/polyethylene glycol (100 EO) stearate mixture (Arlacel 165 FL, ICI) | 2 |
| Stearyl alcohol (Lanette 18, Henkel) | 1 |
| Palm oil stearic acid (Stéarine TP, Stéarinerie Dubois) | 2.5 |
| Polydimethylsiloxane (Dow Corning 200 Fluid, Dow Corning) | 0.5 |
| $C_{12}/C_{15}$ Alkyl benzoate (Witconol TN, Witco) | 20 |
| Triethanolamine | 0.5 |
| Butyl Methoxydibenzoylmethane (Parsol 1789, Hoffmann-LaRoche) | 3 |
| Drometrizole Trisiloxane (Silatrizole, Rhodia Chimie) | 5 |
| Compound of formula (15) | 5 |
| Glycerol | 4 |
| Triethanolamine | 0.3 |
| Polyacrylic acid (Synthalen K, 3V) | 0.4 |
| Preservatives | q.s. |
| Demineralized water q.s. for | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, enhanced SPF cosmetic/dermatological UV-screening composition suited for photoprotecting the skin and/or hair, comprising:

(i) at least one UV-screening benzotriazole-substituted silicon compound,
(ii) at least one UV-screening dibenzoylmethane compound, and
(c) at least one 4,4-diarylbutadiene compound, formulated into a topically applicable, cosmetically/dermatologically acceptable vehicle therefor.

2. The cosmetic/dermatological UV-screening composition as defined by claim 1, the said compounds (i), (ii) and (iii) being present in a proportion as to confer synergistically enhanced SPF activity thereto.

3. The cosmetic/dermatological UV-screening composition as defined by claim 1, said at least one benzotriazole-substituted silicon compound comprising a silane and/or polyorganosiloxane having a benzotriazole functional group substituent and which comprises the following formula (1):

in which $R_7$ is an optionally halogenated $C_1$–$C_{10}$ alkyl radical, or a phenyl radical, or a trimethylsilyloxy radical; $a$ is an integer ranging from 0 to 3, inclusive; and G is a monovalent radical bonded directly to a silicon atom and which corresponds to the following formula (2):

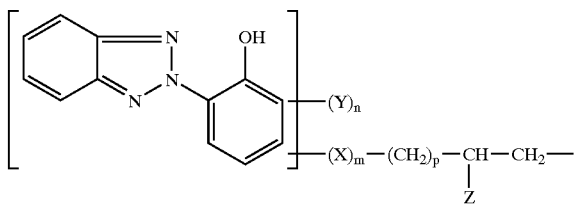

in which the radicals Y, which may be identical or different, are each a $C_1$–$C_8$ alkyl radical, a halogen or a $C_1$–$C_4$ alkoxy radical, with the proviso that, in the latter event, two adjacent Y radicals on the same aromatic nucleus can together form an alkylidenedioxy group in which the alkylidene group has from 1 to 2 carbon atoms; X is O or NH; Z is hydrogen or a $C_1$–$C_4$ alkyl radical; $n$ is an integer ranging from 0 to 3, inclusive; $m$ is 0 or 1, and $p$ is an integer ranging from 1 to 10, inclusive.

4. The cosmetic/dermatological UV-screening composition as defined by claim 3, said benzotriazole-substituted silicon compound having one of the following formulae (5) and (6):

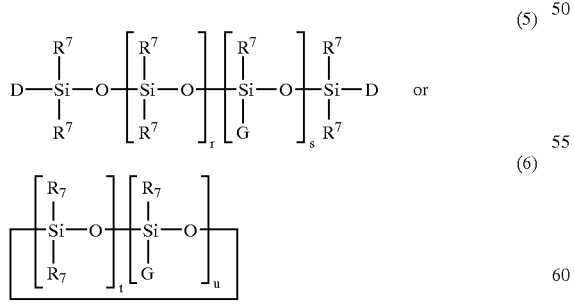

in which the radicals $R_7$, which may be identical or different, are each $C_1$–$C_{10}$ alkyl, phenyl, 3,3,3-trifluoropropyl or trimethylsilyloxy radicals, at least 80% by number of the $R_7$ radicals being methyl; the radicals D, which may be identical or different, are each $R_7$ radicals or the G radical; $r$ is an integer ranging from 0 to 50, inclusive, and s is an integer ranging from 0 to 20, inclusive, and, if $s$=0, at least one of the two radicals D is a radical G; $u$ is an integer ranging from 1 to 6, inclusive, and $t$ is an integer ranging from 0 to 10, inclusive, with the proviso that $t$+$u$ is equal to or greater than 3.

5. The cosmetic/dermatological UV-screening composition as defined by claim 4, said benzotriazole-substituted silicon compound having the following formula (7):

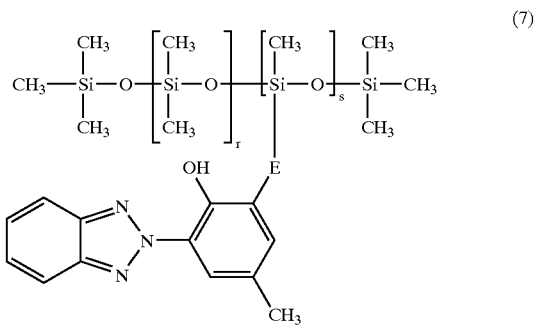

with
0≤r≤10,
0≤s≤10,
and wherein E is the divalent radical:

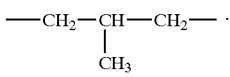

6. The cosmetic/dermatological UV-screening composition as defined by claim 5, said benzotriazole-substituted silicon compound comprising Drometrizole Trisiloxane having the following formula:

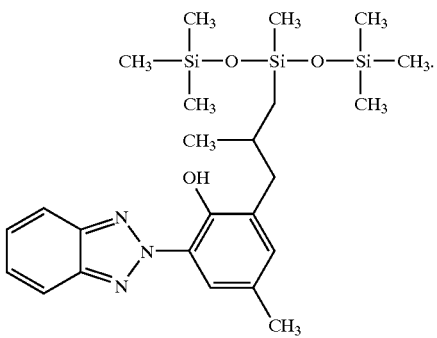

7. The cosmetic/dermatological UV-screening composition as defined by claim 1, said benzotriazole-substituted silicon compound comprising from 0.5% to 15% by weight thereof.

8. The cosmetic/dermatological UV-screening composition as defined by claim 1, said at least one dibenzoylmethane compound being selected from the group consisting of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane, 4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane,
and mixtures thereof.

9. The cosmetic/dermatological UV-screening composition as defined by claim 8, said at least one dibenzoylmethane compound comprising 4-(tert-butyl)-4'-methoxydibenzoylmethane.

10. The cosmetic/dermatological UV-screening composition as defined by claim 8, said at least one dibenzoylmethane compound comprising 4-isopropyldibenzoylmethane.

11. The cosmetic/dermatological UV-screening composition as defined by claim 1, said at least one dibenzoylmethane compound comprising from 0.5% to 15% by weight thereof.

12. The cosmetic/dermatological UV-screening composition as defined by claim 1, said at least one 4,4-diarylbutadiene compound having the following formula (III):

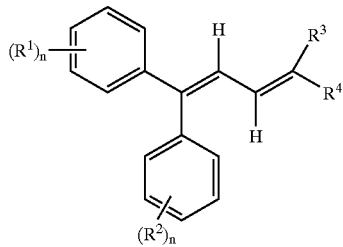

(III)

in which the diene system has the Z,Z; Z,E; E,Z or E,E configuration or is composed of mixtures of the said configurations, and wherein the radicals $R^1$ and $R^2$, which may be identical or different, are each hydrogen; a linear or branched $C_1-C_{20}$ alkyl radical; a $C_2-C_{10}$ alkenyl radical; a $C_1-C_{12}$ alkoxy radical; a $C_3-C_{10}$ cycloalkyl radical; a $C_3-C_{10}$ cycloalkenyl radical; a linear or branched $C_1-C_{20}$ alkoxycarbonyl radical; a linear or branched $C_1-C_{12}$ monoalkylamino radical; a linear or branched di($C_1-C_{12}$) alkylamino radical; an aryl radical; a heteroaryl radical or a water-solubilizing substituent which comprises a carboxylate group, a sulfonate group or an ammonium residue; $R^3$ is a $COOR^5$, $COR^5$, $CONR^5R^6$ or CN group; a linear or branched $C_1-C_{20}$ alkyl radical; a $C_2-C_{10}$ alkenyl radical; a $C_3-C_{10}$ cycloalkyl radical; a $C_7-C_{10}$ bicycloalkyl radical; a $C_3-C_{10}$ cycloalkenyl radical; a $C_7-C_{10}$ bicycloalkenyl radical; a $C_6-C_{18}$ aryl radical; or a $C_3-C_7$ heteroaryl radical; $R^4$ is a $COOR^6$, $COR^6$, $CONR^5R^6$ or CN group; a linear or branched $C_1-C_{20}$ alkyl radical; a $C_2-C_{10}$ alkenyl radical; a $C_3-C_{10}$ cycloalkyl radical; a $C_7-C_{10}$ bicycloalkyl radical; a $C_3-C_{10}$ cycloalkenyl radical; a $C_7-C_{10}$ bicycloalkenyl radical; an aryl radical; or a heteroaryl radical; the radicals $R^5$ and $R^6$, which may be identical or different, are each hydrogen; $[V]_o$—$R^7$; $C_1-C_6$-alkylene-$SO_3U$; $C_1-C_6$-alkylene-$PO_3U$; $C_1-C_6$-alkylene-$N(R^8)_3{}^+A^-$; a linear or branched $C_1-C_{20}$ alkyl radical; a $C_2-C_{10}$ alkenyl radical; a $C_3-C_{10}$ cycloalkyl radical; a $C_7-C_{10}$ bicycloalkyl radical; a $C_3-C_{10}$ cycloalkenyl radical; a $C_7-C_{10}$ bicycloalkenyl radical; an aryl radical; or a heteroaryl radical; V is a —$CH_2$—$CH_2$—W—, —$CH_2CH_2CH_2W$—, —$CH(CH_3)$—$CH_2$—W—, —$CH_2$—$CH_2$—$CH_2$—$CH_2$—W— or —$CH_2$—$CH(CH_2CH_3)$—W— group; A is Cl, Br, I or $SO_4R^9$; U is denotes hydrogen, $Na^+$, $K^+$, $Mg^{2+}$, $Ca^{2+}$, $Li^+$, $Al^{3+}$ or —$N(R^8)_4{}^+$; W is O or NH; the radicals $R^7$ and $R^8$, which may be identical or different, are each hydrogen; a linear or branched $C_1-C_6$ alkyl radical; a linear or branched $C_2-C_6$ alkenyl radical; or a linear or branched $C_1-C_6$ acyl radical; $R^9$ is hydrogen; a linear or branched $C_1-C_6$ alkyl radical; or a $C_2-C_6$ alkenyl radical; n varies from 1 to 3; and o varies from 1 to 150.

13. The cosmetic/dermatological UV-screening composition as defined by claim 12, in which the compound of formula (III) has the following formula (IIIa):

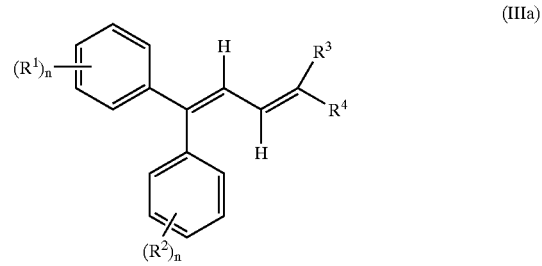

(IIIa)

in which the diene system has the Z,Z; Z,E; E,Z or E,E configuration or is composed of mixtures of the said configurations, and wherein the radicals $R^1$ and $R^2$, which may be identical or different, are each hydrogen; a $C_1-C_8$ alkyl radical; a $C_1-C_8$ alkoxy radical; or a water-solubilizing substituent which comprises a carboxylate group, a sulfonate group or an ammonium residue; $R^3$ is a $COOR^5$, $CONR^5R^6$ or CN group; $R^4$ is a $COOR^6$ or $CONR^5R^6$ group; $R^5$ is hydrogen; $[V]_o$—$R^7$; $C_1-C_6$-alkylene-$SO_3U$; or $C_1-C_6$-alkylene-$N(R^8)_3{}^+A^-$; $R^6$ is $[V]_o$—$R^7$; $C_1-C_6$-alkylene-$SO_3U$; or $C_1-C_6$-alkylene-$N(R^8)_3{}^+A^-$; V is a —$CH_2$—$CH_2$—O—, —$CH_2CH_2CH_2O$— or —$CH(CH_3)$—$CH_2$—O— group; A is Cl, Br, I or $SO_4R^9$; U is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which may be identical or different, are each hydrogen or a linear or branched $C_1-C_3$ alkyl radical; n varies from 1 to 3; and o varies from 0 to 50.

14. The cosmetic/dermatological UV-screening composition as defined by claim 12, in which the compound of formula (III) has the following formula (IIIb):

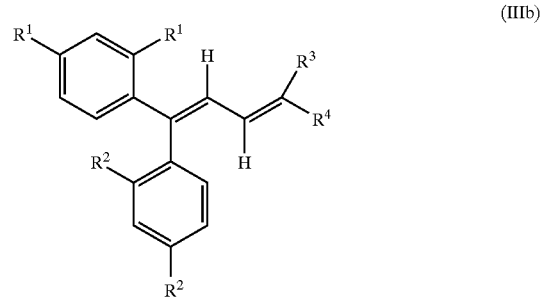

(IIIb)

in which the diene system has the Z,Z; Z,E; E,Z or E,E configuration or is composed of mixtures of the said configurations, and wherein $R^1$ and $R^2$, which may be identical or different, are each hydrogen; a $C_1-C_8$ alkyl radical; or a $C_1-C_8$ alkoxy radical; $R^3$ is a $COOR^5$, $CONR^5R^6$ or CN group; $R^4$ is a $COOR^6$ or $CONR^5R^6$ group; $R^5$ is hydrogen; $[V]_o$—$R^7$; $C_1-C_6$-alkylene-$SO_3U$; or $C_1-C_6$-alkylene-$N(R^8)_3{}^+A^-$; $R^6$ is $[V]_o$—$R^7$; $C_1-C_6$- alkylene-SO$_3$U; or C$_1$–C$_6$-alkylene-N(R$^8$)$_3$$^+$A$^-$; V is a —CH$_2$—CH$_2$—O—, —CH$_2$CH$_2$CH$_2$O— or —CH(CH$_3$)—CH$_2$—O— group; A is Cl, Br, I or SO$_4$R$^9$; U is hydrogen, Na$^+$, K$^+$, Mg$^{2+}$, Ca$^{2+}$, Li$^+$, Al$^{3+}$ or —N(R$^8$)$_4$$^+$; the radicals R$^7$, R$^8$ and R$^9$, which may be identical or different, are each hydrogen or a linear or branched C$_1$–C$_3$ alkyl radical; and o varies from 0 to 50.

15. The cosmetic/dermatological UV-screening composition as defined by claim 12, in which the compound of formula (III) has the following formula (IIIc):

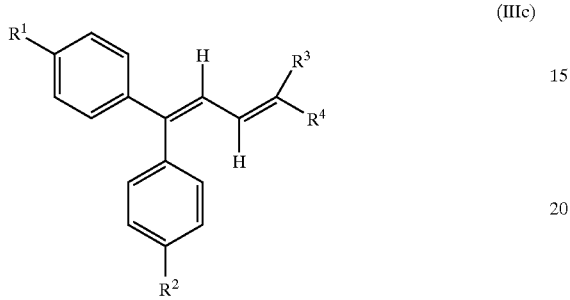

(IIIc)

in which the diene system has the Z,Z; Z,E; E,Z or E,E configuration or is composed of mixtures of the said configurations, and wherein the radicals R$^1$ and R$^2$, which may be identical or different, are each hydrogen; a C$_1$–C$_8$ alkyl radical; or a C$_1$–C$_8$ alkoxy radical; R$^3$ is a COOR$^5$, CONR$^5$R$^6$ or CN group; R$^4$ is a COOR$^6$ or CONR$^5$R$^6$ group; R$^5$ is hydrogen; [V]$_o$—R$^7$; C$_1$–C$_6$-alkylene-SO$_3$U; or C$_1$–C$_6$-alkylene-N(R$^8$)$_3$$^+$A$^-$; R$^6$ is [V]$_o$—R$^7$; C$_1$–C$_6$-alkylene-SO$_3$U; or C$_1$–C$_6$-alkylene-N(R$^8$)$_3$$^+$A$^-$; V is a —CH$_2$—CH$_2$—O—, —CH$_2$CH$_2$CH$_2$O— or —CH(CH$_3$)—CH$_2$—O— group; A is Cl, Br, I or SO$_4$R$^9$; U is hydrogen, Na$^+$, K$^+$, Mg$^{2+}$, Ca$^{2+}$, Li$^+$, Al$^{3+}$ or —N(R$^8$)$_4$$^+$; the radicals R$^7$, R$^8$ and R$^9$, which may be identical or different, are each hydrogen or a linear or branched C$_1$–C$_3$ alkyl radical; and o varies from 0 to 50.

16. The cosmetic/dermatological UV-screening composition as defined by claim 15, in which the 4,4-diarylbutadiene compound is selected from among the following compounds:

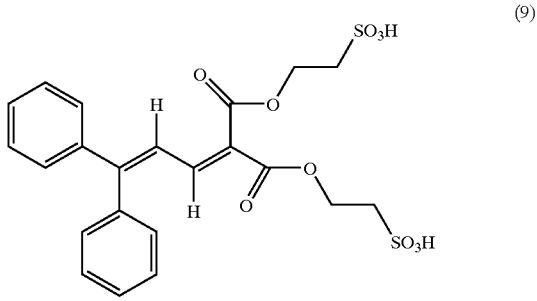

(9)

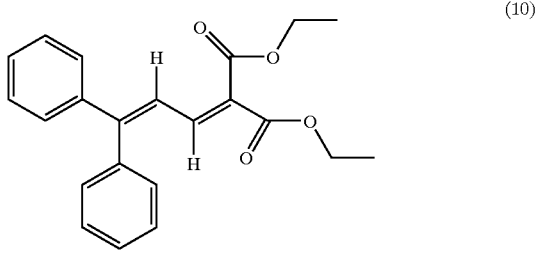

(10)

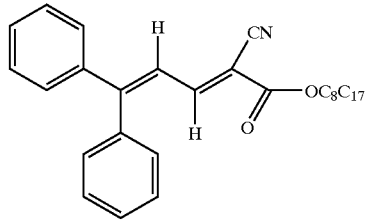

(11)

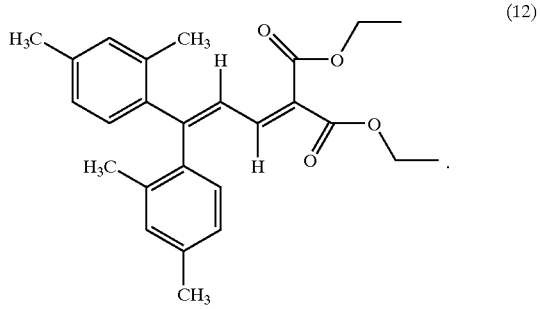

(12)

17. The cosmetic/dermatological UV-screening composition as defined by claim 1, said at least one 4,4-diarylbutadiene compound comprising an oligomer having the following formula (IV):

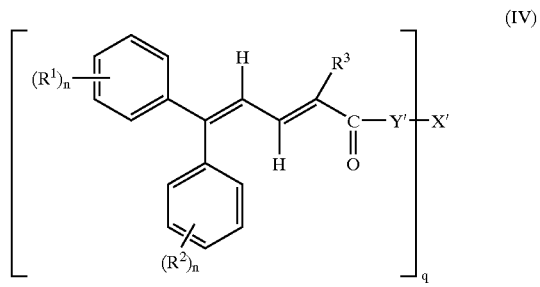

(IV)

in which the diene system has the Z,Z; Z,E; E,Z or E,E configuration or is composed of mixtures of the said configurations, and wherein the radicals R$^1$, R$^2$, R$^3$ and n have the same meanings indicated in the formula (III); Y' is an —O— or —NR$^{10}$— group; R$^{10}$ is hydrogen; a linear or branched C$_1$–C$_{20}$ alkyl radical; a C$_2$–C$_{10}$ alkenyl radical; a C$_3$–C$_{10}$ cycloalkyl radical; a C$_7$–C$_{10}$ bicycloalkyl radical; a C$_3$–C$_{10}$ cycloalkenyl radical; a C$_7$–C$_{10}$ bicycloalkenyl radical; an aryl radical; or a heteroaryl radical; X' is a linear or branched, aliphatic or cycloaliphatic, polyol residue comprising 2 to 10 hydroxyl groups and with a valency of q; with the proviso that the carbonaceous chain of said residue may be interrupted by one or more sulfur or oxygen atoms; one or more imine groups; or one or more C$_1$–C$_4$ alkylimine groups; and q varies from 2 to 10.

18. The cosmetic/dermatological UV-screening composition as defined by claim 17, wherein the oligomer of formula (IV), the radicals R$^1$ and R$^2$, which may be identical or different, are each hydrogen; a C$_1$–C$_{12}$ alkyl radical; a C$_1$–C$_8$ alkoxy radical; or a water-solubilizing substituent which comprises a carboxylate group, a sulfonate group or an ammonium residue; R$^3$ is a COOR$^5$, CONR$^5$R$^6$ or CN group; a C$_3$–C$_{10}$ cycloalkyl radical; or a C$_7$–C$_{10}$ bicycloalkyl radical; the radicals R$^5$ and R$^6$, which may be identical or different, are each a linear or branched C$_1$–C$_{20}$ alkyl radical; a C$_3$–C$_{10}$ cycloalkyl radical; a C$_7$–C$_{10}$ bicycloalkyl radical; or an optionally substituted naphthyl or phenyl; and X' is a polyol residue comprising from 2 to 6 hydroxyl groups.

19. The cosmetic/dermatological UV-screening composition as defined by claim 18, wherein said oligomer of formula (IV), X' is an ethanol or pentaerythritol residue.

20. The cosmetic/dermatological UV-screening composition as defined by claim 17, said at least one oligomer of formula (IV) comprising at least one of:

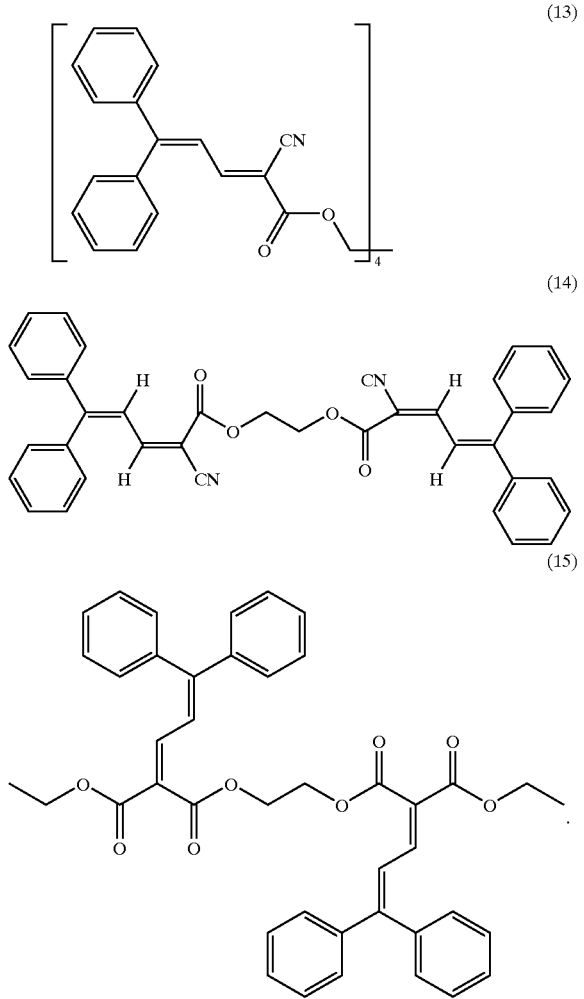

21. The cosmetic/dermatological UV-screening composition as defined by claim 1, said at least one 4,4'-diarylbutadiene compound comprising from 1% to 10% by weight thereof.

22. The cosmetic/dermatological UV-screening composition as defined by claim 1, further comprising at least one other UV-A-active and/or UV-B-active organic screening agent.

23. The cosmetic/dermatological UV-screening composition as defined by claim 22, said at least one organic UV-screening agent being selected from the group consisting of anthranilates; cinnamic derivatives; salicylic derivatives; camphor derivatives; triazine derivatives; benzophenone derivatives; β,β'-diphenylacrylate derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenyl)benzotriazole derivatives; screening polymers and screening silicones; dimers derived from α-alkylstyrene, and mixtures thereof.

24. The cosmetic/dermatological UV-screening composition as defined by claim 23, said at least one other organic UV-screening agent being selected from the group consisting of:
Ethylhexyl salicylate,
Ethylhexyl methoxycinnamate,
Octocrylene,
Phenylbenzimidazolesulfonic acid,
Terephthalylidenedicamphorsulfonic acid,
4-Methylbenzylidenecamphor,
Benzophenone-3,
Benzophenone-4,
Benzophenone-5,
Disodium phenyl dibenzimidazole tetrasulfonate,
Anisotriazine,
Ethylhexyl triazone,
Diethylhexyl butamido triazone,
2,4,6-tris(Diisobutyl 4'-aminobenzalmalonate)-s-triazine,
-Methylenebis(benzotriazolyl)tetramethylbutyl-phenol,
and mixtures thereof.

25. The cosmetic/dermatological UV-screening composition as defined by claim 1, further comprising at least one coated or uncoated metal oxide pigment or nanopigment.

26. The cosmetic/dermatological UV-screening composition as defined by claim 25, said at least one UV-screening pigment or nanopigment comprising titanium oxide, zinc oxide, iron oxide, zirconium oxide, cerium oxide, and mixtures thereof.

27. The cosmetic/dermatological UV-screening composition as defined by claim 1, further comprising at least one agent for artificially tanning and/or browning the skin.

28. The cosmetic/dermatological UV-screening composition as defined by claim 1, further comprising at least one adjuvant or additive selected from the group consisting of fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preservatives, agents, surfactants, anti-inflammatories, substance P antagonists, fillers, polymers, propellants, acidifying or basifying agents, colorants, and mixtures thereof.

29. The cosmetic/dermatological UV-screening composition as defined by claim 1, formulated for photoprotecting the human epidermis and comprising a nonionic vesicular dispersion, an emulsion, a cream, a milk, a gel, a cream-gel, a suspension, a dispersion, a powder, a solid, a mousse or a spray.

30. The cosmetic/dermatological UV-screening composition as defined by claim 1, formulated as a makeup for the eyelashes, the eyebrows or the skin and formulated as solid or pasty, anhydrous or aqueous formulation, or an emulsion, a suspension or a dispersion.

31. The cosmetic/dermatological UV-screening composition as defined by claim 1, formulated for photoprotecting the hair against ultraviolet rays and comprising a shampoo, a lotion, a gel, an emulsion or a nonionic vesicular dispersion.

32. A regime or regimen for photoprotecting the skin and/or hair against the damaging effects of UV radiation, comprising topically applying thereon an effective amount of the cosmetic/dermatological UV-screening composition as defined by claim 1.

33. A method for synergistically enhancing the SPF activity of at least one UV-screening benzotriazole-substituted silicon compound and at least one UV-screening dibenzoylmethane compound, comprising formulating therewith an effective amount of at least one 4,4-diarylbutadiene compound.

* * * * *